(12) United States Patent
O'Brien

(10) Patent No.: US 11,738,142 B2
(45) Date of Patent: Aug. 29, 2023

(54) FLUID PUMP WITH ADAPTIVE FILTER

(71) Applicant: CareFusion 303, Inc., San Diego, CA (US)

(72) Inventor: Kevin O'Brien, Thurles (IE)

(73) Assignee: CareFusion 303, Inc., San Diego, CA (US)

( * ) Notice: Subject to any disclaimer, the term of this patent is extended or adjusted under 35 U.S.C. 154(b) by 346 days.

(21) Appl. No.: 17/191,227

(22) Filed: Mar. 3, 2021

(65) Prior Publication Data

US 2021/0275741 A1 Sep. 9, 2021

Related U.S. Application Data

(60) Provisional application No. 62/986,095, filed on Mar. 6, 2020.

(51) Int. Cl.
*A61M 5/168* (2006.01)
*F04B 49/08* (2006.01)
*F04B 51/00* (2006.01)
*F04B 53/20* (2006.01)

(52) U.S. Cl.
CPC ......... *A61M 5/16854* (2013.01); *F04B 49/08* (2013.01); *F04B 51/00* (2013.01); *F04B 53/20* (2013.01); *A61M 2205/18* (2013.01); *A61M 2205/3344* (2013.01); *A61M 2205/3584* (2013.01); *A61M 2205/50* (2013.01); *A61M 2205/502* (2013.01); *A61M 2205/52* (2013.01); *A61M 2205/587* (2013.01); *A61M 2230/30* (2013.01); *F04B 2205/01* (2013.01); *F04B 2207/042* (2013.01)

(58) Field of Classification Search
CPC ...... A61M 5/16854; A61M 2205/3344; A61M 2205/52; A61M 5/1723; F04B 49/08; F04B 51/00; F04B 53/20; F04B 2205/01
See application file for complete search history.

(56) References Cited

U.S. PATENT DOCUMENTS 10,226,571 B2 3/2019 Davis et al.
2008/0167641 A1 7/2008 Hansen et al.

FOREIGN PATENT DOCUMENTS

| EP | 0 784 493 A1 | 7/1997 |
| EP | 0 923 392 A1 | 6/1999 |
| WO | WO-96/08288 A1 | 3/1996 |
| WO | WO-98/04303 A1 | 2/1998 |
| WO | WO-01/37904 A2 | 5/2001 |

*Primary Examiner* — Bradley J Osinski
(74) *Attorney, Agent, or Firm* — Mintz, Levin, Cohn, Ferris, Glovsky and Popeo, P.C.

(57) ABSTRACT

A method includes measuring a fluid pressure of fluid in a fluid supply line of an infusion pump. The fluid pressure includes a motor pressure and a patient pressure. The method also includes determining the patient pressure. The determining includes removing, by an adaptive filter, to remove the motor pressure from the measured fluid pressure. The removing includes generating a predicted motor pressure based on the current of the motor, generating an error signal based on a comparison between the predicted motor pressure and the measured fluid pressure, and removing the motor pressure from the measured fluid pressure when an error value indicative of the error signal is less than an error threshold. The method also includes adjusting, based on the patient pressure, a setting of the infusion pump. Related methods and articles of manufacture, including apparatuses and computer program products, are also disclosed.

20 Claims, 12 Drawing Sheets

FLUID PUMP WITH ADAPTIVE FILTER

CROSS-REFERENCE TO RELATED APPLICATIONS

The present application claims priority to U.S. Provisional Application No. 62/986,095, filed on Mar. 6, 2020, and entitled "Fluid Pump with Adaptive Filter," the entirety of which is incorporated by reference herein.

TECHNICAL FIELD

The subject matter described herein relates generally to the dispensation of fluids and more specifically to a pump system with an adaptive filter for an infusion device for the delivery of fluid medications.

BACKGROUND

Fluid pumps, such as infusion pumps, administer therapy to patients by delivering a medication or other fluid to the patient. The pumps may be connected with a fluid delivery tube, such as intravenous tubing or other administration sets. Delivery of the fluid may be adjusted based on the fluid pressure within the fluid delivery tube to help ensure that the patient is properly treated. During delivery of the fluid, movement of the patient or other sources may cause the fluid pressure within the fluid delivery tube to fluctuate, which if left unmonitored, may lead to unintended bolus, under-delivery, and/or cessation of the fluid delivered to the patient, causing various medical complications. Determining the changes in the fluid pressure attributable to the movement of the patient or other sources, and adjusting the pump to account for those changes, may be difficult, since the motor of the pump also contributes to the fluid pressure. Sensors and detection methods, such as direct flow-rate measurements, which are used to measure the fluid pressure, may generally be unreliable, inaccurate, and require a significant amount of device resources (e.g., power, processing time, memory, network bandwidth, and the like), especially for low flow rates of the fluid delivered to the patient.

SUMMARY

Systems, methods, and articles of manufacture, including computer program products, are provided for using an adaptive filter with a fluid pump, such as an infusion pump, to separate contributors to fluid pressure of fluid within a fluid delivery tube coupled with the fluid pump. The systems described herein more effectively adjust one or more fluid pump settings for improved feed-forward control of the fluid pump and reduction of unintended boluses, under-delivery, and/or cessation of fluid flow within the fluid delivery tube due to changes in downstream pressure.

According to some aspects, a method includes measuring a fluid pressure of fluid in a fluid supply line of an infusion pump. The fluid pressure may include a motor pressure and a patient pressure. The method may also include determining the patient pressure. The determining may include removing, by an adaptive filter, to remove the motor pressure from the measured fluid pressure. The removing may also include generating a predicted motor pressure based on the current of the motor, generating an error signal based on a comparison between the predicted motor pressure and the measured fluid pressure, and removing the motor pressure from the measured fluid pressure when an error value indicative of the error signal is less than an error threshold. The method also includes adjusting, based on the patient pressure, a setting of the infusion pump.

In some aspects, the removing also includes generating a predicted motor pressure based on the current of the motor. The removing may also include generating an error signal based on a comparison between the predicted motor pressure and the measured fluid pressure. The removing may further include removing the motor pressure from the measured fluid pressure when an error value representative of the error signal is less than an error threshold.

In some aspects, the current of the motor is stored in a shift register of the adaptive filter.

In some aspects, the adaptive filter is a digital adaptive filter.

In some aspects, the comparison between the predicted motor pressure and the measured fluid pressure is a difference between the predicted motor pressure and the measured fluid pressure.

In some aspects, the error value is one or more of a norm of the error signal and a least means square of the error signal.

In some aspects, generating the error signal further includes applying a tap filter coefficient to the error value.

In some aspects, the removing further includes determining whether the error value is less than an error threshold. In some aspects, the removing further includes determining that the error value is greater than or equal to the threshold value. The removing may also include adjusting one or more filter coefficients of the filter. The one or more filter coefficients may be applied to the current of the motor. In some aspects, the removing may also include generating an updated predicted motor pressure based on the adjusted one or more filter coefficients and the current of the motor.

In some aspects, the removing further includes: generating an updated error signal based on a comparison between the updated predicted motor pressure and the measured fluid pressure. The removing may also include determining that an updated error value indicative of the updated error signal is less than the error threshold.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a pump system having an adaptive filter, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
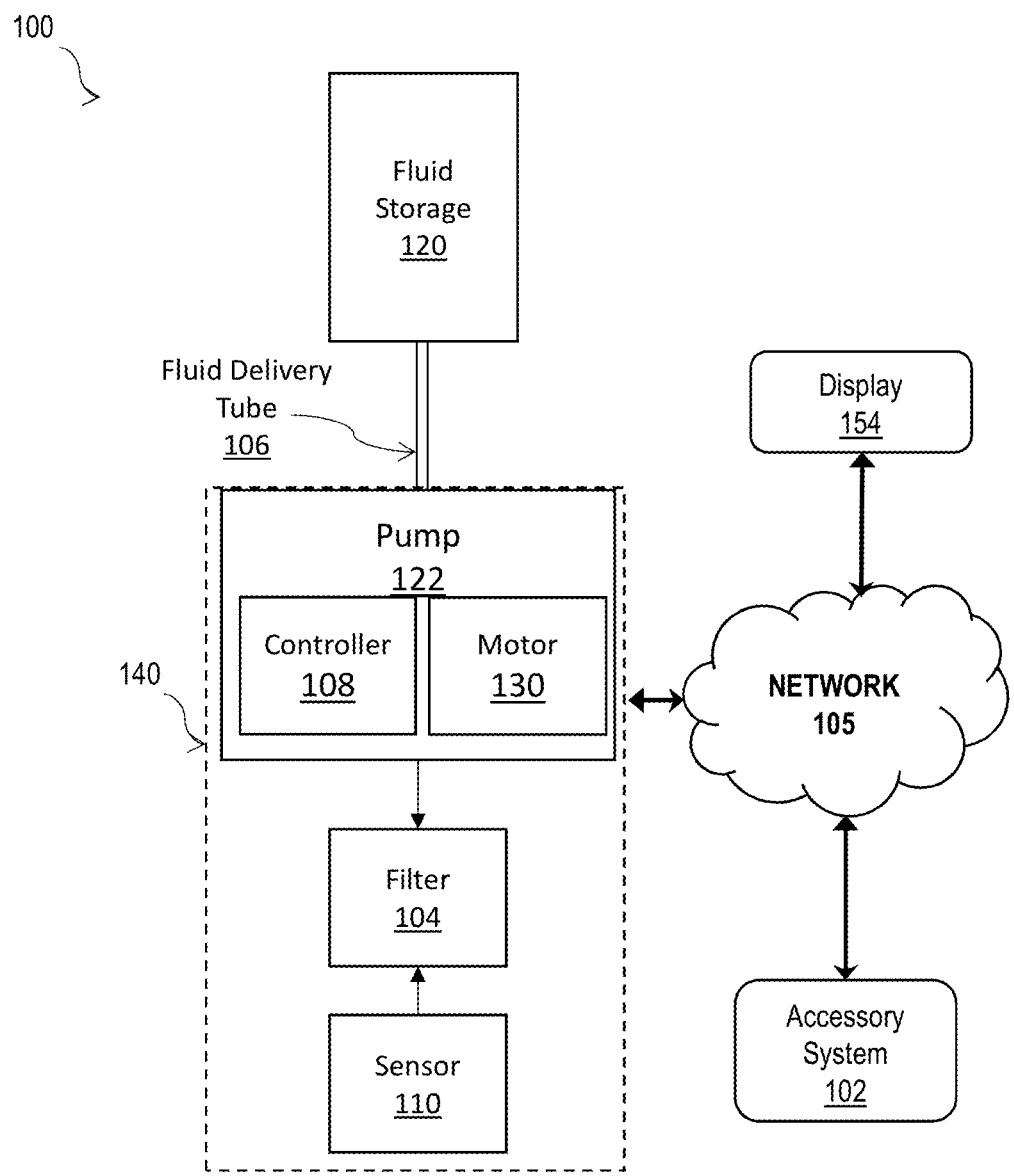
FIG. 1 depicts a system diagram illustrating a pump system, in accordance with some example embodiments.

Fluid pumps, such as infusion pumps, administer therapy to patients by delivering a medication or other fluid to the patient. The fluid pumps may be connected with a fluid delivery tube, such as intravenous tubing or other administration sets. Various parameters of the fluid delivery by the fluid pumps may be adjusted based on the fluid pressure of the fluid passing through the fluid delivery tube to help ensure that a proper amount of fluid is delivered to the patient. During use of the fluid pumps, movement of the patient, or other sources may cause the fluid pressure within the fluid delivery tube to fluctuate, which if left unmonitored, may lead to unintended bolus, under-delivery, and/or cessation of the fluid delivered to the patient, thereby causing various medical complications. Determining the changes in the fluid pressure attributable to the movement of the patient, or other sources, and adjusting the pump to account for those changes, may be difficult, since the motor of the pump also contributes to the fluid pressure. Sensors and detection methods for measuring the fluid pressure, such as direct flow-rate measurements, may generally be unreliable, inaccurate, and require a significant amount of device resources (e.g., power, processing time, memory, network bandwidth, and the like), especially for low flow rates of the fluid delivered to the patient.

The pump system described herein may employ an adaptive filter to improve the accuracy in detecting the changes in fluid pressure attributable to the movement of the patient or other sources (without the pump motor), which helps to reliably adjust pump settings for improved feed-forward control of the pump and reduction of unintended boluses, under-delivery, and/or cessation of fluid delivered to the patient. An adaptive filter may be a digital or analogue filter that has self-adjusting characteristics. For example, an adaptive filter may be capable of adjusting (e.g., continuously and/or at various time intervals) one or more coefficients of the filter to adapt or otherwise improve the accuracy of an input signal, such as one or more motor current measurements. In some implementations, the adaptive filter is adjusted until the error (e.g., a difference between an output of the filter and the desired signal) is minimized and the filter converges to an optimal state. For example, as the adaptive filter adapts its coefficients, the error converges to its minimal value. When the error converges to its minimal value, the adaptive filter has been adapted and the coefficients of the filter have converged to an output (e.g., the motor pressure, patient pressure, and/or the like). In some implementations, the adaptive filter is a filter system that includes one or more (e.g., one, two, three, four, or more) filters, such as linear filters variable filters, least means squares filters, recursive least squares filters, and/or the like.

Incorporating an adaptive filter in the context of the pump system described herein may be especially useful when delivering fluid to a patient using a pump, as pumps (e.g., a motor of the pump) may impact fluid pressure signal readings corresponding to fluid within the fluid delivery tube, by creating a significant amount of noise in the fluid pressure signal. The pump system incorporating the adaptive filter described herein may help to reduce or eliminate the noise produced by the pump from the fluid pressure signal to provide fluid pressure signals with improved accuracy, reliability, and efficiency. As a result, the pump system may desirably provide improved feed-forward control of the pump and reduce unintended boluses, under-delivery, and/or cessation of fluid delivered to the patient.

Accordingly, in some examples, the adaptive filter used in the pump system may help to separate contributors to the fluid pressure signal, such as the pump motor contribution, patient contribution, and/or the like. For example, the adaptive filter may determine, by comparing signals representing movement of the pump motor (which may be determined based on the motor current or another method) to pressure sensor readings, accurately predicting a component of the pressure sensor readings that may be attributed to the pump motor by applying thresholds to various filter coefficients of the adaptive filter, and removing the contributions by the pump motor from the pressure sensor readings. After the pump motor contributions have been removed from the fluid pressure sensor readings, the residual component of the fluid pressure is due to patient movement, venous pressure, or other sources external to the pump. As a result, one or more pump settings may be adjusted, based on the residual component of the fluid pressure, to control the delivery of fluid to the patient. Thus, the adaptive filter combined with the pump described herein may improve control of the pump, and reduce or eliminate unintended boluses, under-delivery, and/or cessation of fluid delivery to the patient due to changes in downstream pressure. In some embodiments, the removal of the pump motor contribution to the fluid pressure signal may allow for more useful information to be extracted based on the fluid pressure signal due to the reduction in noise created by the pump motor. Additionally and/or alternatively, improved down-stream pressure feed-forward control of the pump system including the adaptive filter described herein may help to reduce or eliminate the level of bolus or under-infusion of fluid delivery due to changes in elevation, and the fluid flow rate of the fluid in the fluid delivery tube may quickly return to a desired flow rate in a short amount of time.

FIG. 1 depicts a system diagram illustrating a pump system 100, in accordance with some example embodiments. Referring to FIG. 1, the pump system 100 may include a fluid storage 120, a pump filter system 140 that includes a pump (also referred to herein as an "infusion device") 122, a filter 104, and a sensor 110, a fluid delivery tube 106 connecting the fluid storage 120 and the pump 122, a network 105, an accessory system 102, and a display 154. In some example embodiments, the display 154, the filter 104, the sensor 110, and/or the accessory system 102 may form a portion of the pump 122 and/or may be positioned within a housing of the pump 122.

The display 154 may form a part of the pump 122 or may be separately coupled as part of a client device. The display 154 may also include a user interface. The user interface may form a part of a display screen of the display 154 that presents information to the user and/or the user interface may be separate from the display screen. For example, the user interface may be one or more buttons, or portions of the display screen that is configured to receive an entry from the user. The client device may be a mobile device such as, for example, a smartphone, a tablet computer, a wearable apparatus, and/or the like. However, it should be appreciated that the client device may be any processor-based device including, for example, a desktop computer, a laptop computer, a workstation, and/or the like. Via the display 154, the user may be able to configure certain parameters of the pump 122, such as a filter coefficient threshold, a desired flow rate or flow rate limit, an alarm limit, and/or the like. Additionally, in some examples, via the display 154, the user may configure various fluid protocols with default settings and safety parameters (e.g., setting a limit to a dose of a fluid).

The accessory system 102 may include an alarm, light (e.g., an LED), a sound source, and/or other indicator. The indicator may indicate to the user of one or more measurements, thresholds, or other detected events relating to the pump 122. For example, the indicator may indicate to the user that a fluid pressure within the fluid delivery tube 106 is greater than, less than, or equal to a threshold, a rate of change of the fluid pressure is greater than, less than, or equal to a threshold, the measured fluid pressure does not match a desired fluid pressure, a coefficient of a filter is greater than, less than, or equal to a threshold, and the like. As noted above, the accessory system 102 may form a part of the pump 122 and/or the display 154, or may be separately coupled to the pump 122, such as via the network 105.

As FIG. 1 shows, the pump filter system 140 (e.g., the pump 122, the filter 104, and/or the sensor 110), the display 154, and/or the accessory system 102 may be communicatively coupled via a network 105. The network 105 may be any wired and/or wireless network including, for example, a public land mobile network (PLMN), a local area network (LAN), a virtual local area network (VLAN), a wide area network (WAN), the Internet, and/or the like.

The pump 122 may be any type of pump configured to move a fluid from a fluid storage 120, such as a reservoir, drip chamber, syringe, and/or the like, through a conduit or other tube, such as fluid delivery tube 106, to a destination (not shown) such as, for example, a patient. The pump 122 may be a Large Volume Infusion Pump (LVP), a syringe pump (SP), an anesthesia delivery pump, infusion pump and/or a patient-controlled analgesic (PCA) pump configured to deliver a medication to a patient. However, it should be appreciated that the pump 122 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like. Additionally and/or alternatively, the pump 122 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like. Additionally and/or alternatively, the pump 122 may include a pump that is coupled to a down-stream pressure sensor. Moreover, the pump 122 may be part of a patient care system that includes one or more additional pumps.

The pump 122 may include a controller 108 and a motor 130. The motor 130 may include various types of motors, such as electric motors, and the like. The motor 130 may control a fluid flow rate of the fluid passing through the fluid delivery tube 106 to be delivered to the patient. The motor 130 may include a motor current, which corresponds to the fluid flow rate. The controller 108 may determine and/or control the fluid flow rate, such as a level of the fluid flow rate, changes in the fluid flow rate, and/or the like by adjusting the current provided to the motor. For example, in some embodiments, the controller 108 receives a desired value and/or rate of change of the fluid flow rate selected via the display 154.

In some embodiments, the controller 108 may determine the value and/or rate of change of the fluid flow rate based at least in part on one or more sensor readings from the sensor 110. The sensor 110 may be coupled with the pump 122 and/or the filter 104. The sensor 110 may include a downstream pressure sensor positioned on or near the patient, such as at or near a fluid delivery site. In some embodiments, the sensor 110 measures a fluid pressure of fluid within the fluid delivery tube 106. The sensor 110 may make fluid pressure readings continuously and/or at various time intervals (e.g., every 10 seconds, 30 seconds, 1 minute, 30 minutes, 1 hour, 12 hours, 24 hours, and the like). In some embodiments, the controller 108 controls the time at which the sensor 110 measures the fluid pressure. The sensor 110 may transmit the fluid pressure readings to the filter 104 and/or to the pump 122 (e.g., the controller 108). As noted above, the fluid pressure may include one or more pressure signals caused by one or more components of the pump system 100, patient movement, venous pressure, and/or the like. In some embodiments, the controller 108 may communicate with one or more other systems, such as the accessory system 102, the display 154, and/or the filter 104.

The filter 104 may include one or more digital and/or analog filters. For example, the filter 104 may include an adaptive filter, which as noted above, may help to separate the contributors to the fluid pressure signal, such as the pump contribution, patient contribution, and/or the like. The adaptive filter 104 may be capable of adjusting (e.g., continuously and/or at various time intervals) various coefficients of the filter to adapt or otherwise improve the accuracy of a fluid pressure signal. For example, in some embodiments, the filter 104 described herein may help to reduce or eliminate the noise produced by the pump 122

(e.g., the motor 130 of the pump 122) from the fluid pressure signal to provide fluid pressure signals that are caused by patient movement, venous pressure, and/or the like. In other words, the filter 104 described herein may accurately provide a fluid pressure signal that does not include the noise (or pressure signals) caused by the pump 122 (e.g., the motor 130 of the pump 122). In some embodiments, as described in more detail below, the filter 104 may include a least means square ("LMS") predictor to further improve the accuracy of the fluid pressure signal. As a result, the pump system 100 including the filter 104 may desirably improve feed-forward control of the pump and reduce unintended boluses, under-delivery, and/or cessation of fluid delivered to the patient.

Figure 2:
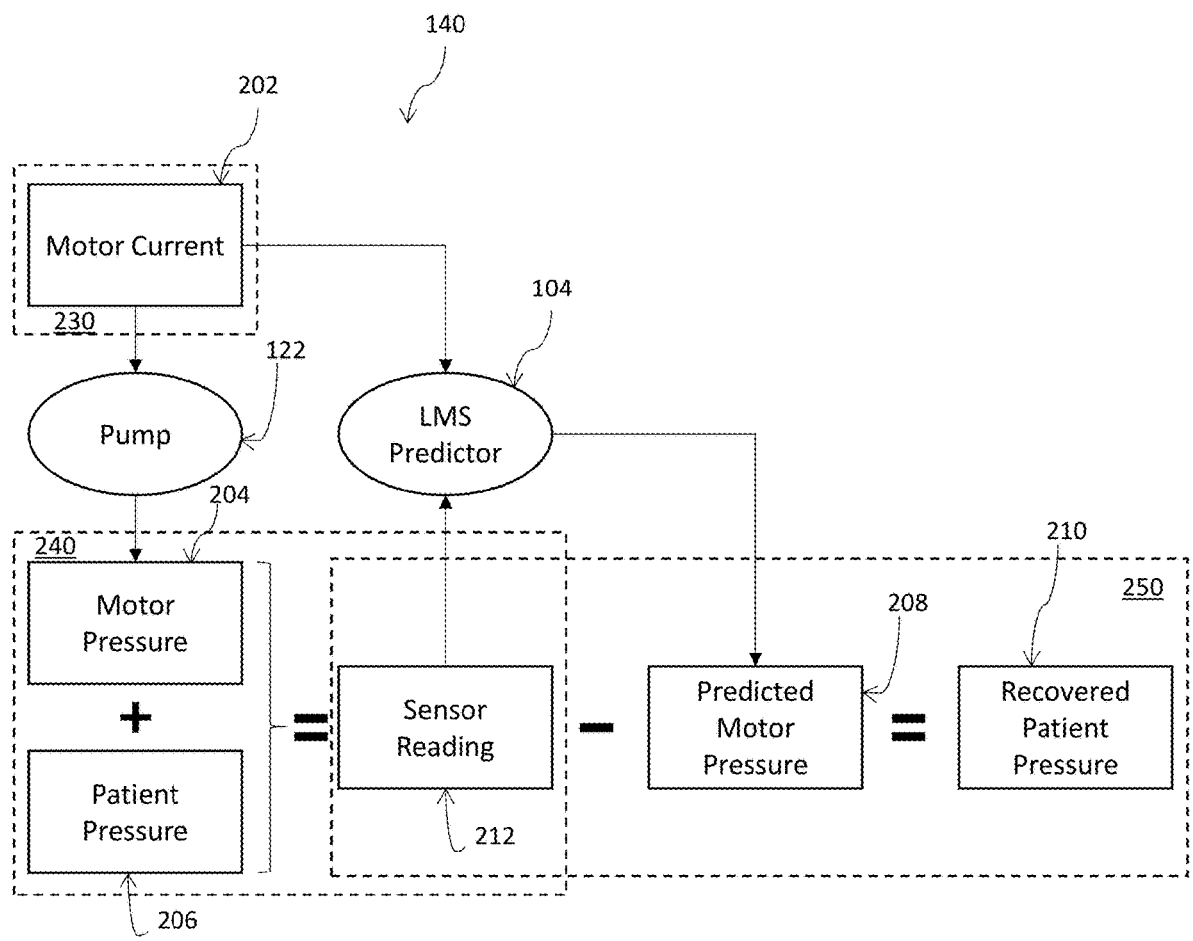
FIG. 2 schematically depicts an example pump, in accordance with some example embodiments.
Figure 3A:
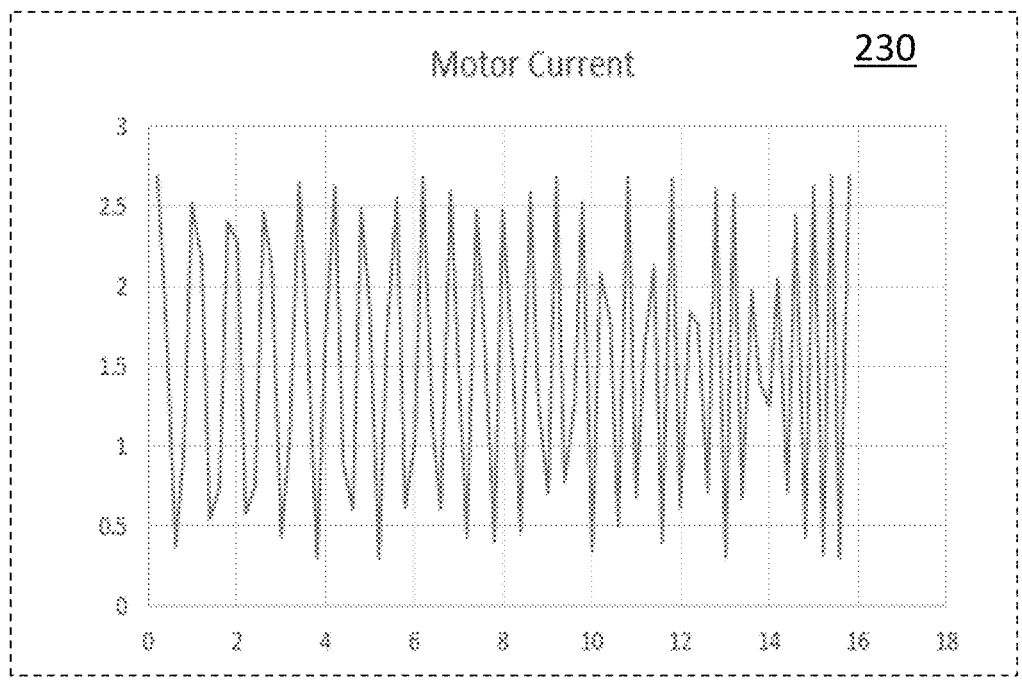
FIGS. 3A-3C depict graphs showing example readings from the pump, in accordance with some example embodiments.
Figure 3B:
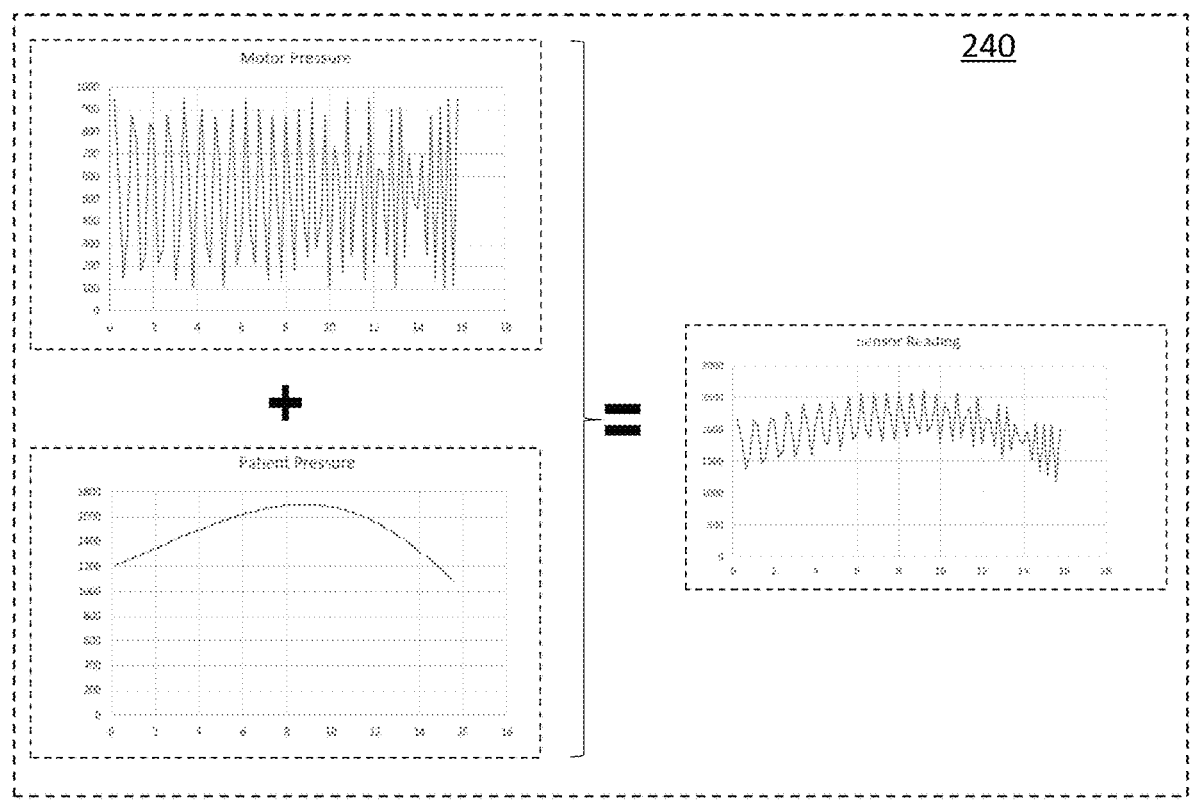
Figure 3C:
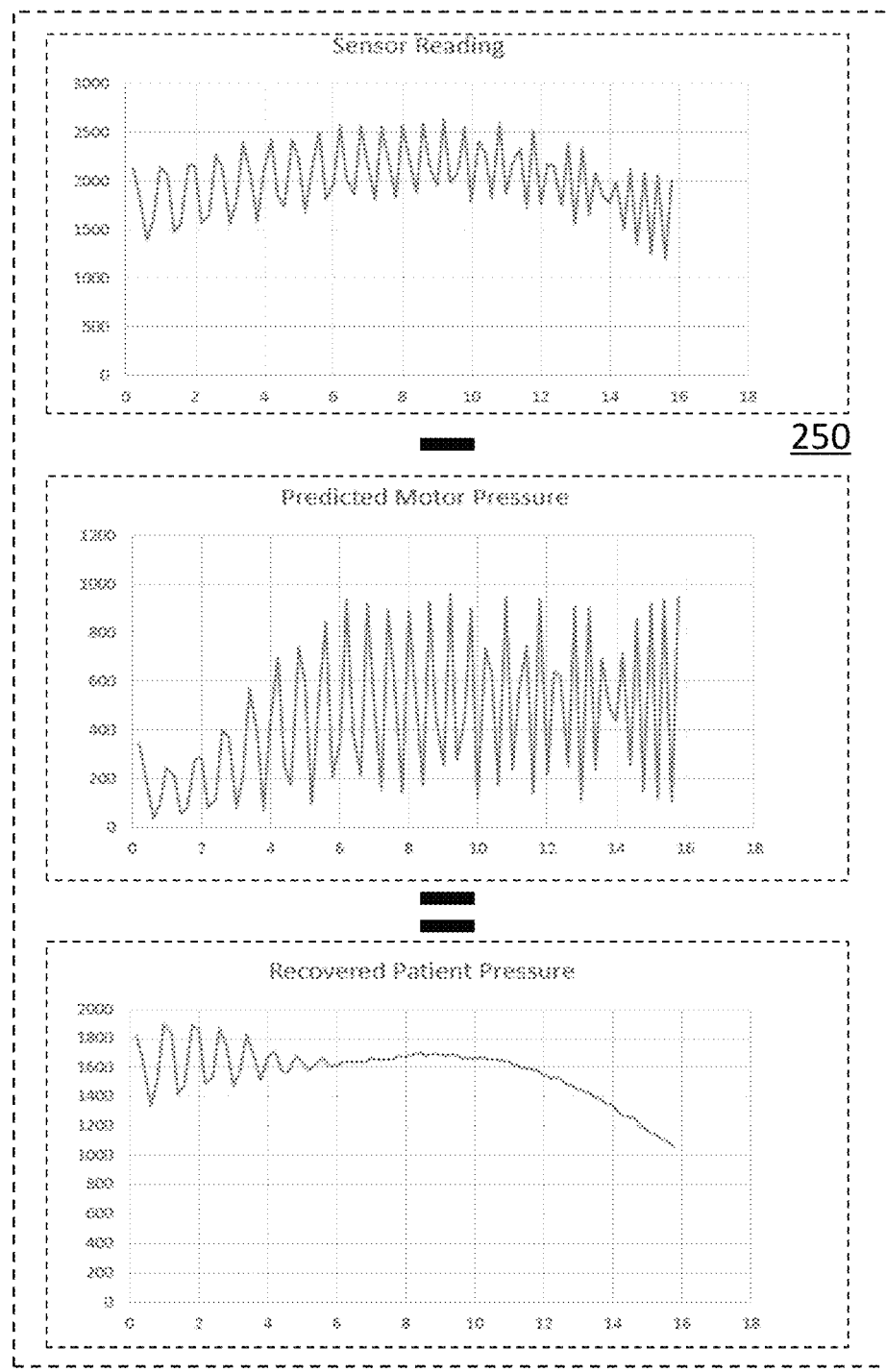
Figure 4A:
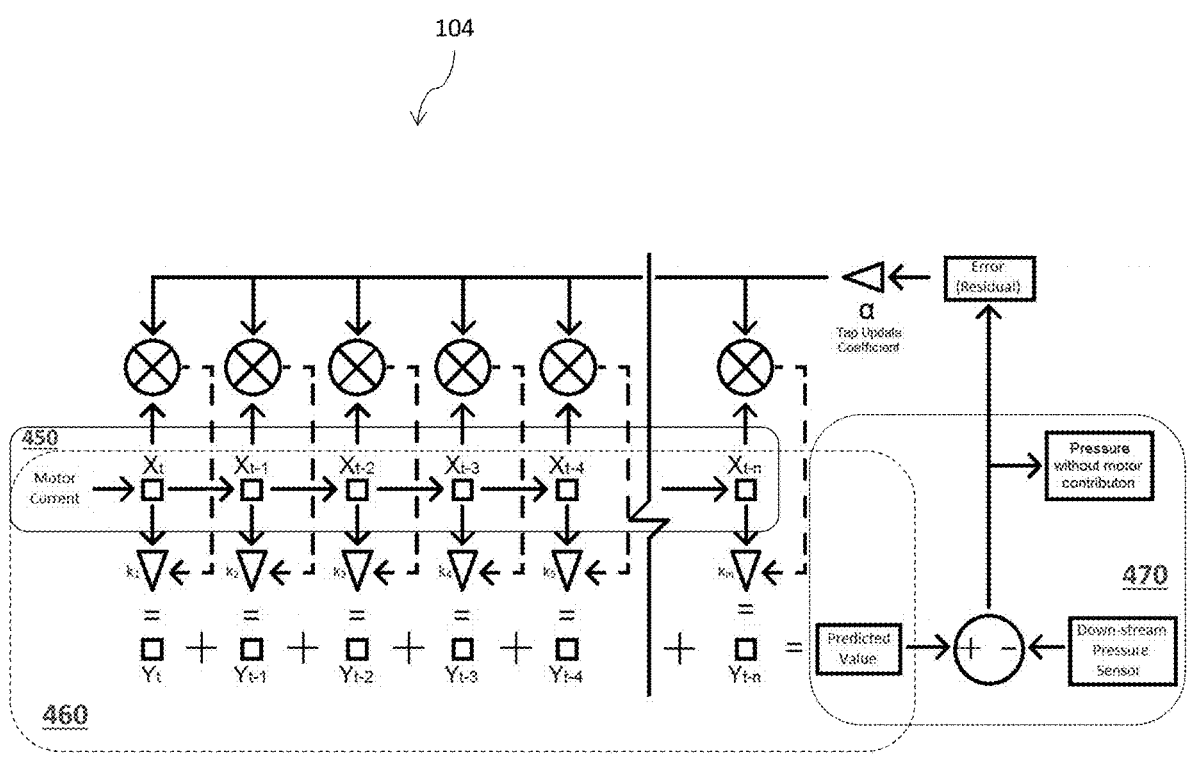
FIGS. 4A-4B schematically depict an adaptive filter and a predictor coupled with the pump, in accordance with some example embodiments.
Figure 4B:
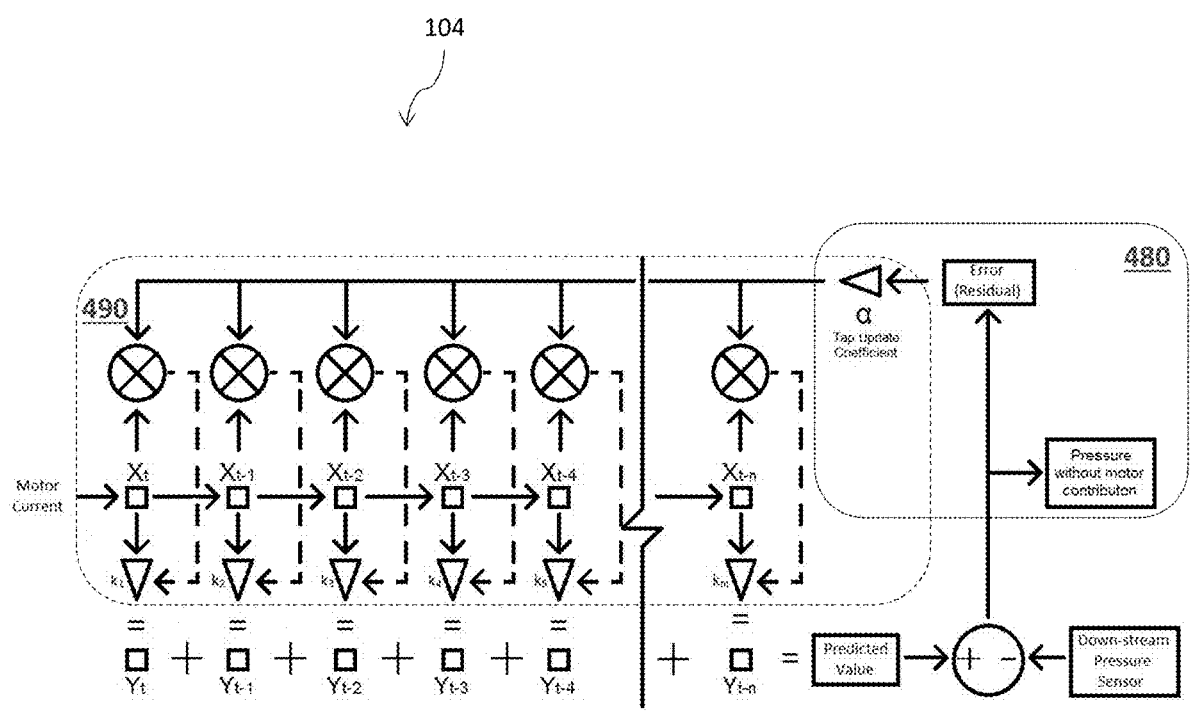

FIG. 2 illustrates a flow diagram that schematically illustrates operation of the pump filter system 140. FIGS. 3A-3C illustrate various graphs that show examples of signals that may be measured by one or more sensors, such as the sensor 110, and/or calculated by the pump filter system 140, such as by the controller 108 of the pump 122. FIGS. 4A-4B schematically illustrate an example of the filter 104, consistent with implementations of the current subject matter.

Referring to FIG. 2, at 230, a motor current 202 is supplied to the motor 130 of the pump 122. The amount of the motor current 202 supplied to the motor 130 may be controlled by the controller 108. In some embodiments, the amount of motor current 202 supplied to the motor 130 may be measured by one or more sensors. In other embodiments, the amount of motor current 202 supplied to the motor 130 may be detected using a back-end Electromagnetic Field ("EMF") reader, a motor current sensor, a motor torque sensor, and/or the like. FIG. 3A illustrates a graph showing a signal that includes a plurality of motor currents 202, at 230, over a period of time (e.g., approximately 16 seconds). As explained in more detail below, the signal representing the motor current 202 may be used by the controller 108 and/or the filter 104 to remove the motor contributions to the fluid pressure in the fluid delivery tube 106.

At 240, the sensor 110, such as one or more pressure sensors, may measure a fluid pressure of the fluid within the fluid delivery tube 106. The sensor 110 may be positioned downstream relative to the pump 122. In some embodiments, the sensor 110 may be positioned on or near the patient, such as at or near a fluid delivery site. The sensor 110 may make fluid pressure readings continuously and/or at various time intervals (e.g., every 10 seconds, 30 seconds, 1 minute, 30 minutes, 1 hour, 12 hours, 24 hours, and the like). In some embodiments, the controller 108 controls the time at which the sensor 110 measures the fluid pressure. The sensor 110 may also transmit the fluid pressure readings to the filter 104 and/or to the pump 122 (e.g., the controller 108). The fluid pressure (and components of the fluid pressure, such as a motor pressure and a patient pressure) may include one or more fluid pressure measurements. In some embodiments, the fluid pressure may be defined by a fluid pressure signal that includes one or more fluid pressure measurements. In some embodiments, the fluid pressure may be defined by a value representing the fluid pressure signal.

The fluid pressure may include one or more pressure signals caused by one or more components of the pump system 100, patient movement, venous pressure, and/or the like. In some embodiments, as shown in FIG. 2 and FIG. 3B, the fluid pressure readings may be a combination of at least a motor pressure 204 and a patient pressure 206. For example, the motor pressure 204 may form a first component of the fluid pressure caused by the motor 130 of the pump 122. The motor 130 generates a torque that is proportional to the motor current 202 supplied to the motor 130. The torque generated by the motor 130 generates the first component (e.g., the motor pressure 204) of the fluid pressure within the fluid delivery tube 106. The patient pressure 206 may form another component of the fluid pressure that is caused by the patient. For example, movement of the patient, venous pressure of the patient, and/or the like may generate the patient pressure 206 of the fluid pressure within the fluid delivery tube 106. As a result, the fluid pressure is a combination of one or more pressures generated by different sources. As an example, FIG. 3B graphically illustrates the fluid pressure signal, the patient pressure signal, and the motor pressure signal. For example, as shown in FIG. 3B, the fluid pressure at 240 (e.g., the fluid pressure signal) may be a combination of the motor pressure 204 (e.g., the motor pressure signal) and the patient pressure 206 (e.g., the patient pressure signal). As shown, the motor pressure 204 has a similar graphical appearance as the motor current 202, since the motor torque is proportional to the motor current 202 supplied to the motor 130.

As shown in FIG. 2, the motor current 202 and the fluid pressure readings 212 may be transmitted (through a wired and/or wireless connection) to the filter 104, which may determine a value of the patient pressure 206 (e.g., a recovered patient pressure 210) at 250, by generating a predicted motor pressure 208 and removing the predicted motor pressure 208 from the fluid pressure readings 212.

FIGS. 4A and 4B schematically depict an example of the filter 104, consistent with implementations of the current subject matter. As noted above, the filter 104 may include a digital and/or analog adaptive filter to separate contributors to the fluid pressure, such as the motor pressure 204 and the patient pressure 206. For example, the filter 104 may first receive and store one or more motor current measurements (e.g., the motor current 202 and/or motor torque). The measurements of the motor current 202 may be loaded into a shift register 402 of the filter 104 with a motor current sample size of n+1, where n is equal to the previous number of motor current measurements. In some embodiments, for example, the motor current sample size is equal to 10 to 20 motor current measurements, which may be taken continuously and/or at predetermined time intervals. In some embodiments, the motor current sample size is equal to the previous 5 to 10 motor current measurements, 10 to 15 motor current measurements, 15 to 20 motor current measurements, 20 to 25 motor current measurements, 10 motor current measurements, 15 motor current measurements, 20 motor current measurements, and/or other ranges therebetween. As an example, FIG. 4A shows the motor current measurements loaded onto the shift register 402 at 450. Each of the motor current measurements are represented, in FIG. 4A showing the filter 104, as $X_t, X_{t-1}, X_{t-2}, X_{t-3}, X_{t-4} \ldots X_{t-n}$.

Next, the filter 104 (or controller 108) may determine a portion of the fluid pressure attributed to the patient pressure 206 by removing (e.g., filtering) the motor pressure 204 from the fluid pressure readings 212. In some embodiments, the filter 104 may generate a first predicted motor pressure based on the motor current measurements loaded onto the shift register 402. For example, the filter 104 may use the below equation to determine a first predicted motor pressure.

$$\Sigma(X_{t \ldots t-n})(k_{1 \ldots m}) = \Sigma(Y_{t \ldots t-n}) \qquad \text{Equation 1:}$$

As noted above, $X_{t \ldots t-n}$ represents each of the motor current measurements. At 460 shown in FIG. 4A, each of the motor current measurements stored in the shift register of the filter 104 are scaled by a corresponding coefficient $k_1 \ldots k_m$. The results of each scaling are represented by $Y_{t \ldots t-n}$, which are combined to provide a first predicted motor pressure.

At 470, the filter 104 (or controller 108), may compare the first predicted motor pressure to the fluid pressure measured by the sensor 110. The controller 108 may compare the first predicted motor pressure to the measured fluid pressure by taking the difference between the first predicted motor pressure and the measured fluid pressure. The difference between the first predicted motor pressure and the measured fluid pressure is equivalent to an error signal, at 480 (see FIG. 4B), which represents the fluid pressure without the motor pressure. In other words, the error signal is equal to the actual patient pressure (the residual component of the fluid pressure after the motor pressure has been removed), once the first predicted motor pressure and the fluid pressure readings converge. Convergence between the first predicted motor pressure and the fluid pressure readings over time indicates that an accurate representation of the fluid pressure attributed to the patient pressure has been determined. An example of the convergence is shown in FIG. 3C. As shown in FIG. 3C, at 250, the predicted motor pressure and the fluid pressure readings begin to converge after approximately 6 seconds. Once the predicted motor pressure and the fluid pressure readings converge, the patient pressure signal is graphically represented by a line with minimal variations (e.g., values of peaks and valleys of each fluctuation are within 0 to 0.5%, 0.5% to 1.0%, 1.0% to 1.5%, 1.5% to 2.0%, 2.0% to 3% or ranges therebetween, of one another).

Before the predicted motor pressure and the fluid pressure readings converge to define the patient pressure, the error signal determined at 480 (see FIG. 4B) may be used to update a tap update coefficient $\alpha$ of the filter 104 at 490 (see FIG. 4B). The tap update coefficient $\alpha$ may be updated based on the error signal by the LMS Predictor of the filter 104 to minimize the least means squared error of the error signal. In some embodiments, however, the tap update coefficient may be constant. The LMS Predictor of the filter 104 may additionally and/or alternatively scale the error signal by applying the tap update coefficient $\alpha$ to the error signal and combining the scaled error signal with the filter coefficients $k_1 \ldots k_m$ for each of the motor current measurements $X_{t \ldots t-n}$. Accordingly, in some embodiments, the error signal may be determined using the following equation:

$$\text{Scaled Error Signal} = (\text{Error Signal} * \alpha) + k_{1 \ldots m} \quad \text{Equation 2:}$$

Additionally, using the scaled error signal, the filter 104 may determine the predicted motor pressure by using the following:

$$\alpha * \Sigma(X_{t \ldots t-n})(k_{1 \ldots m}) = \Sigma(Y_{t \ldots t-n}) \quad \text{Equation 3:}$$

In some embodiments, the filter 104 (such as via the controller 108) may apply various thresholds to the filter coefficients $k_1 \ldots k_m$ to determine the state of the pump system 100. For example, the filter coefficients $k_1 \ldots k_m$ may be updated until an error value representative of the error signal (or scaled error signal) is less than or equal to an error threshold. In some embodiments, the error value is the least means square of the error signal (or scaled error signal), a norm representative of the error signal (or scaled error signal), and/or the like. The error threshold may be 0.1 to 0.2, 0.2 to 0.3, 0.3 to 0.4 or higher. For example, if the error value is greater than or equal to the error threshold, the filter 104 may update or otherwise change the filter coefficients $k_1 \ldots k_m$, which may then be applied to the motor current measurements. In contrast, if the error value is less than the error threshold, the filter 104 may stop updating the filter coefficients $k_1 \ldots k_m$. In this case, the error signal would be equal to the patient pressure and the predicted motor value would be equal to the actual motor pressure.

In some embodiments, the filter 104 (such as via the controller 108) iterates through various filter coefficients to minimize the error value representing the error signal to provide an estimate of the predicted motor pressure value. For example, if the error signal generated between the first predicted motor pressure value and the fluid pressure readings is greater than or equal to the error threshold over a threshold number of cycles (e.g., one, two, three, four, five, ten, fifteen, twenty, or more iterations), the filter 104 may update the filter coefficients $k_1 \ldots k_m$. If the error signal generated between the next predicted motor pressure value determined based on the updated filter coefficients $k_1 \ldots k_m$ and the fluid pressure readings is still greater than or equal to the error threshold after the next iteration, the filter 104 may continue to update the filter coefficients $k_1 \ldots k_m$.

The filter 104 may continue to iterate through various filter coefficients until the error value is less than the error threshold and/or until the number of iterations by the filter 104 has reached the threshold number of cycles. For example, the filter 104 may iterate through various filter coefficients $k_1 \ldots k_m$ by incrementing the filter coefficients $k_1 \ldots k_m$ each time the error value is greater than or equal to the error threshold. The filter 104 may increment the filter coefficients $k_1 \ldots k_m$ by a set amount each iteration (e.g., by 0.1, 0.2, 0.3, 0.4, and the like). In other embodiments, the filter 104 may increment the filter coefficients $k_1 \ldots k_m$ dynamically each iteration, based on the size of the error value relative to the error threshold. For example, the filter 104 may increment the filter coefficients $k_1 \ldots k_m$ by a greater or lesser amount when there is a large difference between the error value and the error threshold (e.g., a difference being greater than or equal to 0.2, 0.3 0.4, and/or the like) and a greater or lesser amount when there is a small difference between the error value and the error threshold (e.g., a difference being less than or equal to 0.2, 0.15, and the like), such as when the predicted motor pressure value and the measured fluid pressure approach convergence.

In some embodiments, upon convergence (e.g., when the error value is less than the error threshold), the resulting transfer function including the filter coefficients at the time of convergence may accurately represent the relationship between the motor current and the pressure sensor readings. In other words, the resulting filter coefficients at the time of convergence may be taken as a digital numerical representation of the motor pressure to fluid pressure transfer function. The transfer function may be used by the controller 108 to determine various parameters of various components of the pump system 100, such as the motor 130, the motor sensor, the pump 122, the fluid delivery tube 106, the sensor 110, and/or the like.

If instead, the error value does not fall below the error threshold within the threshold number of cycles, the controller 108 may ignore the predicted motor pressure value, and instead rely on the fluid pressure including both the motor pressure 204 and the patient pressure 206 to adjust one or more settings of the pump 122 (as described in more detail below). In some embodiments, if the error value does not fall below the error threshold within the threshold number of cycles, the controller 108 of the pump 122 may adjust a user interface, light, or audio component to present a human-perceivable indication that the total fluid pressure of fluid in the fluid delivery tube is being used by the controller 108 to adjust one or more settings of the pump 122. As another example, the pump 122 may disable a pumping mechanism or engage an occluder to stop flow of fluid to the patient from within the fluid delivery tube when the error value does not fall below the error threshold within the threshold number of cycles. In some embodiments, the pump 122 may communicate with the local or wireless accessory system (e.g., the accessory system 102), such as via the display 154 of the pump or separate client device to indicate that the total fluid pressure of fluid in the fluid delivery tube is being used by the controller 108 to adjust one or more settings of the pump 122 and/or that the pump is preventing flow of fluid to the patient. For example, the pump 122 may display an indicator, such as an alarm, text, flashing lights, and/or the like.

In some embodiments, the filter coefficients $k_1 \ldots k_m$ may be tracked over time by the filter 104 (such as via the controller 108). Tracking the filter coefficients $k_1 \ldots k_m$ over time may provide useful information about the status of the pump system 100 (e.g., about the pump 122). For example, changes (e.g., increases or decreases) in the filter coefficients over time may indicate that the pump system 100 is malfunctioning, that preventative maintenance or service on the pump system 100 is required and/or the like. Additionally and/or alternatively, a sudden change (e.g., increase or decrease) in the filter coefficients may indicate that the pump system 100 is malfunctioning, that preventative maintenance or service on the pump system 100 is required and/or the like. When the controller 108 determines that the pump system 100 is malfunctioning and/or that preventative maintenance or service on the pump system 100 is required, the pump 122 may display an indicator as described herein, and/or otherwise disable the pump 122.

Based on the filtered fluid pressure (e.g., the fluid pressure without the motor pressure 204), the controller 108 may adjust one or more settings of the pump 122, such as a speed of the fluid flow or delivery rate, an amount of fluid delivered to the patient, a type of fluid delivered to the patient and/or the like. The pump system 100 including the filter 104 described herein may desirably more accurately adjust the one or more settings of the pump 122 based on more accurate fluid pressure readings. This helps to improve feed-forward control of the pump 122 and reduce or eliminate unintended boluses, under-delivery, and/or cessation of fluid flow within the fluid delivery tube 106 due to changes in the fluid pressure.

Figure 5:
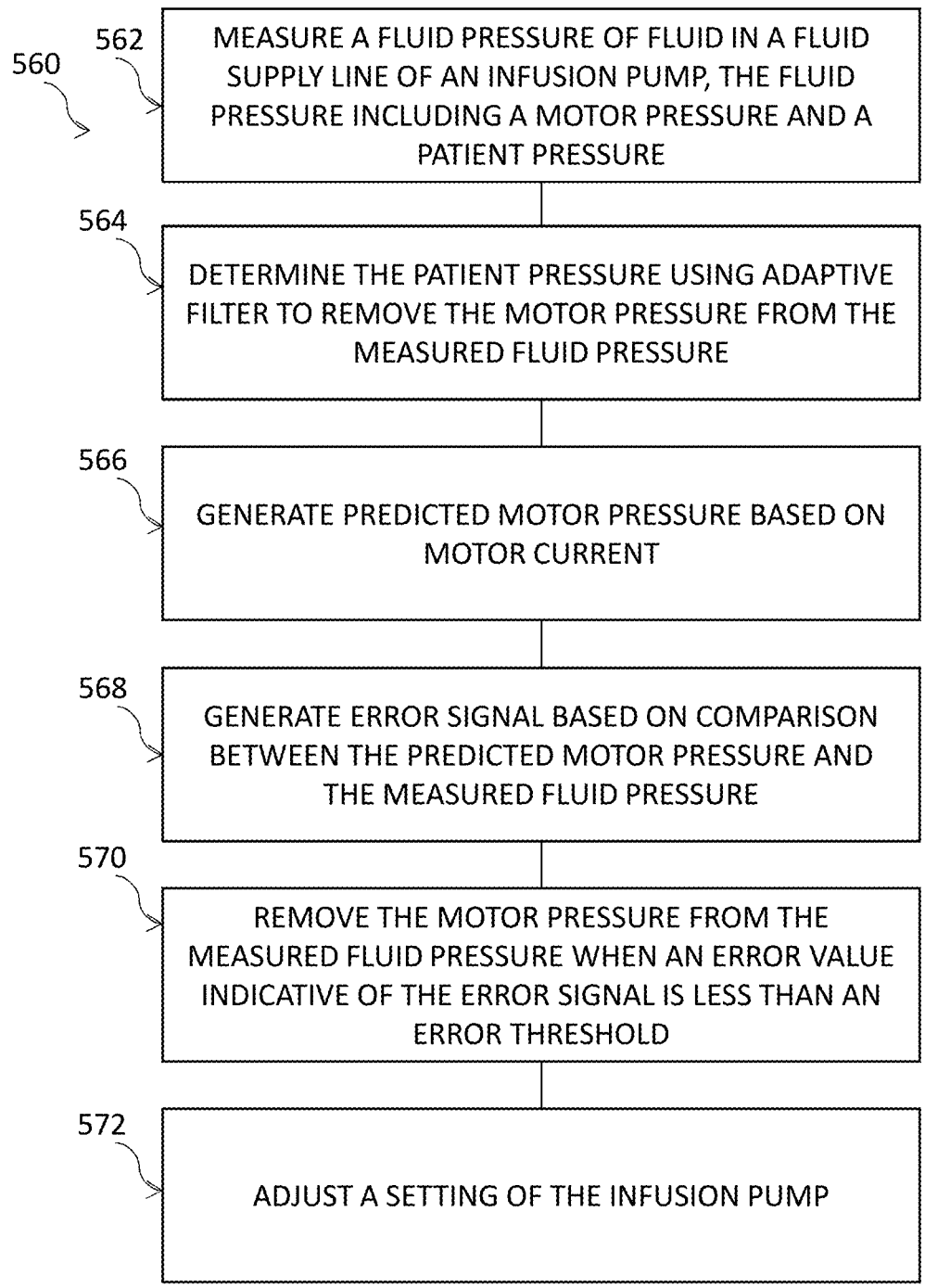
FIG. 5 depicts a flow diagram for adjusting a pump setting based on a patient pressure component of a fluid pressure, in accordance with some example embodiments.

FIG. 5 depicts a flowchart illustrating a process 560 for adjusting a pump setting based on a patient pressure component of a fluid pressure.

At 562, a pressure sensor (such as sensor 110) may measure a fluid pressure of fluid in a fluid supply line (e.g., fluid delivery tube 106) of a fluid pump (e.g., pump 122), such as an infusion pump. The fluid pressure may include a pressure caused by one or more components of the pump and/movements by the patient. For example, the fluid pressure may include a motor pressure caused at least in part by a current of a motor (e.g., the motor 130) of the pump. In some embodiments, the fluid pressure may additionally and/or alternatively include a patient pressure caused at least in part by movement of the patient. The fluid pressure may additionally and/or alternatively include a pressure caused by one or more other sources, such as a venous pressure of the patient, movement of the pump, movement of the fluid supply line, and/or movement of one or more other components of the pump.

As noted above, it may be desirable to remove the motor pressure from the fluid pressure to allow the pump (e.g., via a controller such as controller 108) to more accurately and reliably delivery a fluid (e.g., a desired fluid flow rate, amount of fluid, and the like) to the patient. For example, at 564, the controller, which may be coupled to the pressure sensor, may determine the patient pressure. The controller may accurately and/or reliably determine one or more settings of the pump based on the patient pressure, or at least by removing the motor pressure from the fluid pressure. To determine the patient pressure of the fluid pressure, an adaptive filter (e.g., the filter 104), coupled to the pressure sensor and the controller, may be used to effectively remove the motor pressure from the measured fluid pressure. In some embodiments, the adaptive filter is a digital and/or analog adaptive filter. The adaptive filter may, as described herein, iterate through various filter coefficients to filter the fluid pressure and remove the motor pressure from the fluid pressure over a number of cycles.

At 566, to remove the motor pressure from the measured fluid pressure, the adaptive filter and/or the controller may generate a predicted motor pressure based on the current of the motor. For example, a back-end EMF reader, a motor current sensor, a motor torque sensor, and/or the like, may measure one or more motor currents over a period of time, such as 10 to 20 seconds, continuously and/or at predetermined time intervals. In some embodiments, 10 to 20 motor current measurements are taken and recorded by the back-end EMF reader, a motor current sensor, a motor torque sensor, and/or the like. The motor current measurements may be stored in a data store, such as a shift register (e.g., shift register 402) of the filter 104.

In some embodiments, the predicted motor pressure may be determined by applying one or more filter coefficients to each of the motor current measurements stored on the shift register and combining the scaled motor current measurements. In other words, the combination of the motor current measurements scaled by the filter may represent the initial predicted motor pressure.

At 568, the adaptive filter and/or the controller may generate an error signal based on a comparison between the predicted motor pressure and the measured fluid pressure. For example, adaptive filter and/or the controller may take a difference between the predicted motor pressure and the measured fluid pressure to determine the error signal. As noted above with respect to FIGS. 1-4B, the error signal is representative of the patient pressure component of the fluid pressure when the predicted motor pressure and the fluid pressure signals converge (see FIG. 3C). In other words, the error signal is representative of the patient pressure component of the fluid pressure when there are minimal variations between the predicted motor pressure and the fluid pressure signals.

At 570, the adaptive filter and/or the controller may remove the motor pressure from the measured fluid pressure when an error value representing the error signal is less than an error threshold. For example, the error value may be a norm of the error signal, a least means square of the error signal, and/or another value representing the error signal. In some embodiments, a tap filter coefficient is applied to the error signal and combined with the filter coefficients to determine the error value. In some embodiments, the tap filter coefficient may be applied to the error signal and combined with the filter coefficients by a LMS Predictor of the adaptive filter. The tap filter coefficient may be constant over the number of cycles, or may be dynamically updated after each cycle (e.g., after each iteration).

In some embodiments, removing the motor pressure from the measured fluid pressure includes first determining whether the error value is less than the error threshold. For example, the filter and/or the controller may compare the error value to the error threshold. As an example, based on the comparison between the error value and the error threshold, the filter and/or the controller may determine that the error value is greater than or equal to the error threshold. When the error value is greater than or equal to the error threshold, the one or more filter coefficients may be adjusted and the adjusted filter coefficients may be applied to the motor current measurements. For example, the filter coefficients may be incremented by a predetermined amount and/or may be dynamically updated based on the size of the difference between the error value and the error threshold. The filter and/or the controller may then generate an updated predicted motor pressure based on the adjusted filter coefficients and the current of the motor. The filter and/or the controller may continue to iterate through and adjust the value of the filter coefficients until the filter and/or the controller determines that the error value is less than the error threshold and/or until a predetermined number of iterations (e.g., cycles) have been performed. When the error value is less than the error threshold, the error signal is approximately equal to the desired patient pressure.

If a predetermined number of iterations have been performed before the filter and/or the controller determines that the error value is less than the error threshold, the pump system may make changes to the parameters of the fluid delivery (e.g., a fluid flow rate, an amount of fluid delivered, a type of fluid delivered, and the like) based on the measured fluid pressure. In such instances, the controller may communicate with the accessory system to display an indicator, such as an alarm, text, flashing lights, and/or the like. In some embodiments, the controller may disable a pumping mechanism or engage an occluder to stop flow of fluid to the patient from within the fluid delivery tube when the error value does not fall below the error threshold within the threshold number of iterations.

At 572, the controller may adjust one or more settings of the pump, based at least in part on the determined patient pressure (e.g., the fluid pressure with the motor pressure removed). For example, the controller may adjust one or more settings of the pump, such as a speed of the fluid flow or delivery rate, an amount of fluid delivered to the patient, a type of fluid delivered to the patient and/or the like. The pump system including the adaptive filter described herein may desirably accurately adjust the one or more settings of the pump based on more accurate fluid pressure readings, which helps to improve feed-forward control of the pump and reduce or eliminate unintended boluses, under-delivery, and/or cessation of fluid flow within the fluid delivery tube due to changes in the fluid pressure.

Figure 6:
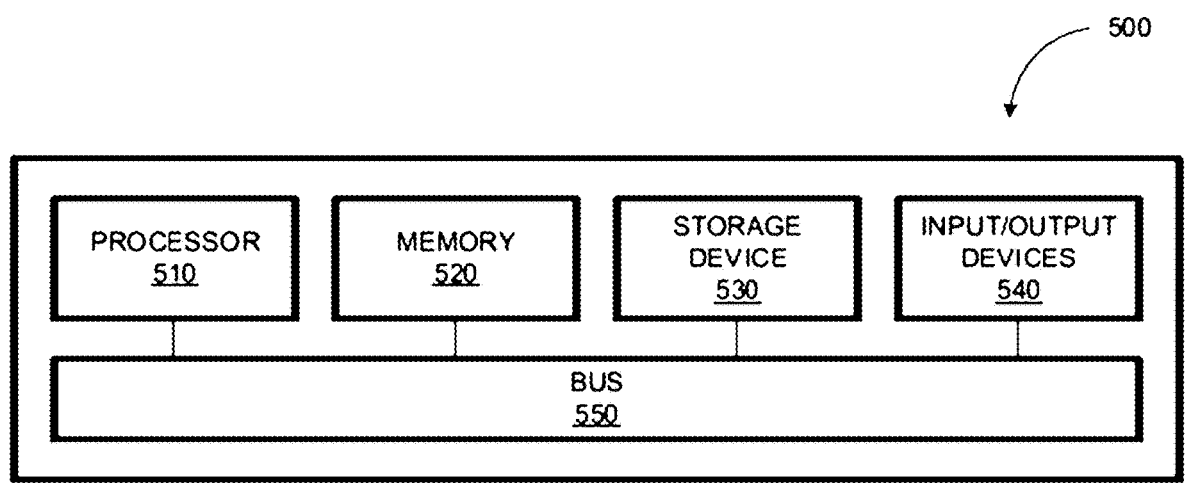
FIG. 6 depicts a block diagram illustrating a computing system, in accordance with some example embodiments.

FIG. 6 depicts a block diagram illustrating a computing system 500 consistent with implementations of the current subject matter. Referring to FIGS. 1 and 6, the computing system 500 can be used to implement the pump filter system 140 (including the pump 122, the filter 104, and the pressure sensor 110), the accessory system 102, the display 154, and/or any components therein.

As shown in FIG. 6, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the pump 122. In some example embodiments, the processor 510 can be a single-threaded processor. Alternatively, the processor 510 can be a multi-threaded processor.

The processor 510 is capable of processing instructions stored in the memory 520 and/or on the storage device 530 to present graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, or a tape device, or other suitable persistent storage means. The input/output device 540 provides input/output operations for the computing system 500. In some example embodiments, the input/output device 540 includes a keyboard and/or pointing device. In various embodiments, the input/output device 540 includes a display unit for displaying graphical user interfaces.

According to some example embodiments, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example embodiments, the computing system 500 can be used to execute various interactive computer software applications that can be used for organization, analysis and/or storage of data in various formats. Alternatively, the computing system 500 can be used to execute software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

Figure 7A:
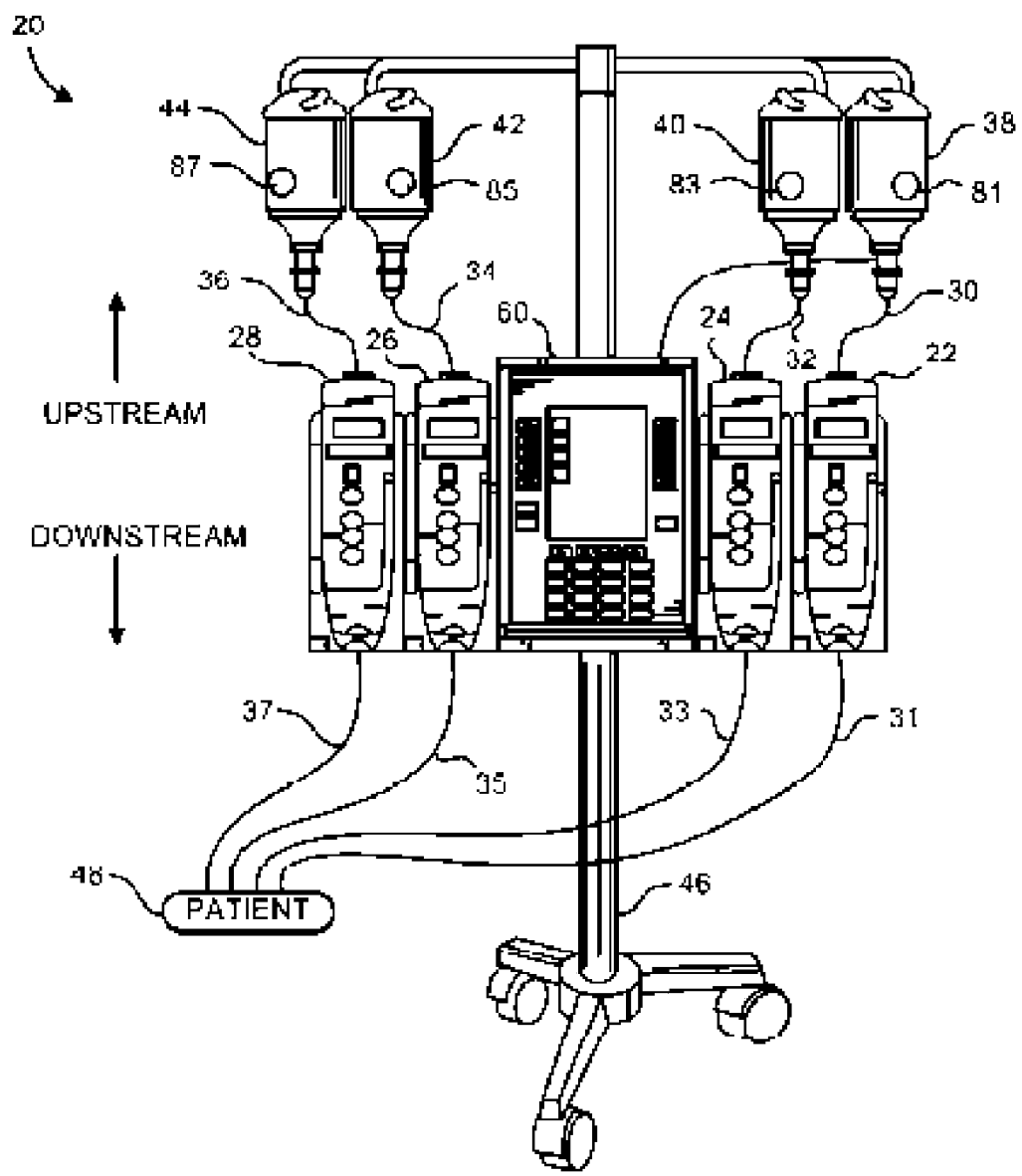
FIG. 7A depicts a front view of a patient care system, in accordance with some example embodiments.
Figure 7B:
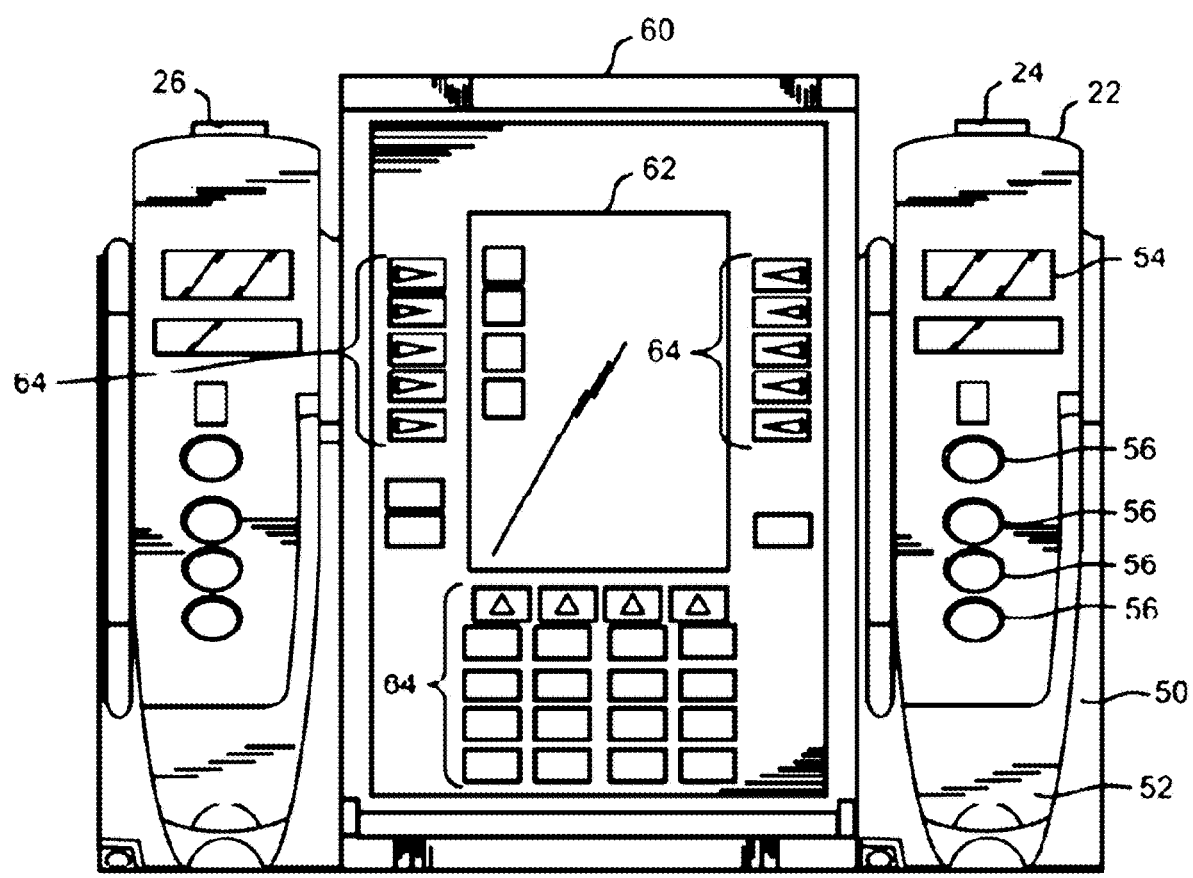
FIG. 7B depicts an enlarged view of a portion of a patient care system, in accordance with some example embodiments.
Figure 7C:
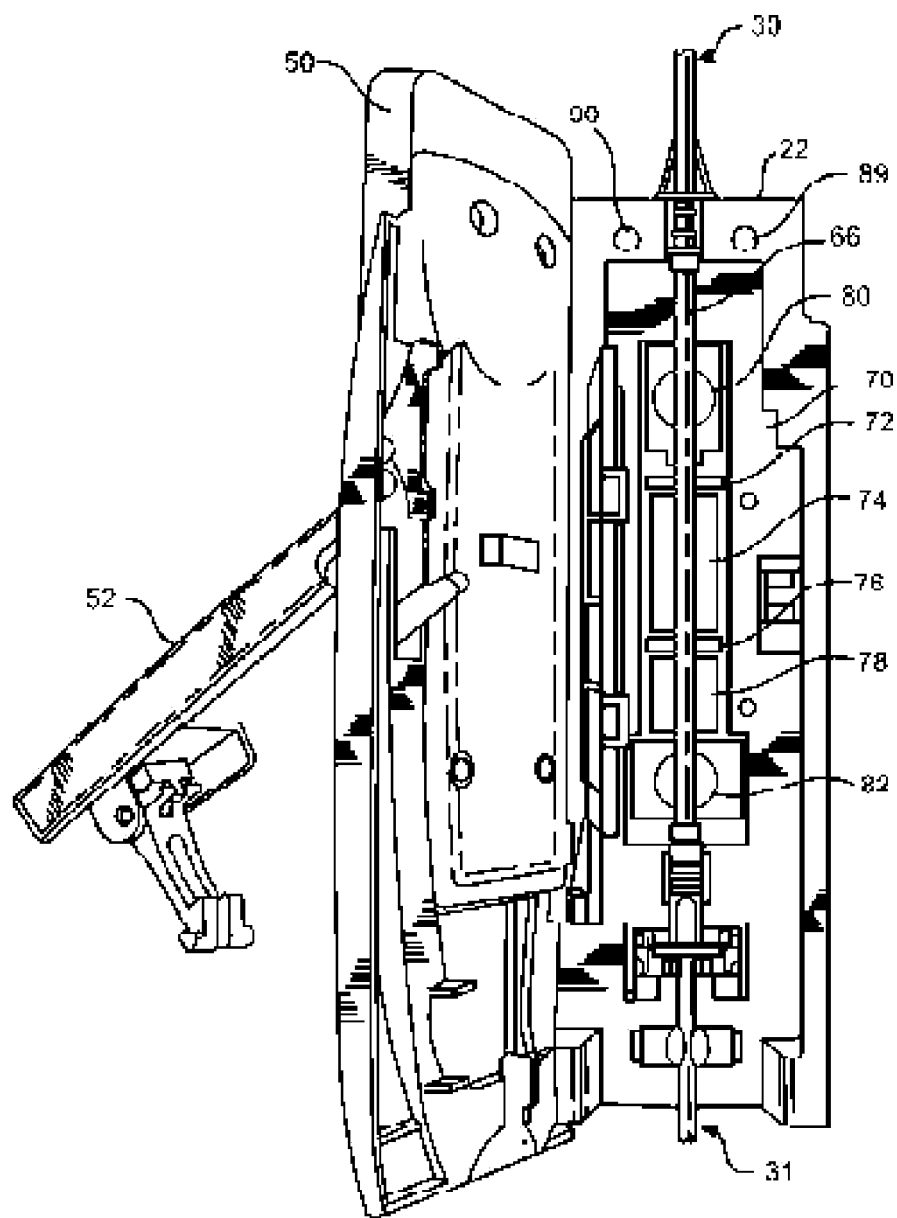
FIG. 7C depicts a perspective view of a pump, in accordance with some example embodiments.

In some example embodiments, the pump 122 (e.g., pump 22 as shown in FIGS. 7A-7C) may be part of a patient care system 20. FIGS. 7A-7C illustrate example embodiments of the patient care system 20, though other types of patient care systems may be implemented. Referring to FIG. 7A, the patient care system 20 may include the pump 22 as well as additional pumps 24, 26, and 28. Although a large volume pump (LVP) is illustrated, other types of pumps may be implemented, such as a small volume pump (SVP), a syringe pump, an anesthesia delivery pump, and/or a patient-controlled analgesic (PCA) pump configured to deliver a medication to a patient. The pump 22 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like, or the pump 22 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like.

As shown in FIG. 7A, each of the pump 22, 24, 26, and 28 may be fluidly connected with an upstream fluid line 30, 32, 34, and 36, respectively. Moreover, each of the four pumps 22, 24, 26, and 28 may also fluidly connected with a downstream fluid line 31, 33, 35, and 37, respectively. The fluid lines can be any type of fluid conduit, such as fluid delivery tube (e.g., the fluid delivery tube 106), through which fluid can flow. At least a portion of one or more of the fluid lines may be constructed with a multi-layered configuration as described herein. In some embodiments, each of the pumps 22, 24, 26, and 28 may use the same fluid line. In such embodiments, as described above, the pump system may detect when various types of fluid flow through the fluid line. In some embodiments, the pump 22 may be coupled to an adaptive filter (e.g., the filter 104), which may remove various components of fluid pressure measured from within the fluid delivery tube, such as the motor pressure caused by operation of a motor of the pump. This helps to improve feed-forward control of the pump and reduce unintended boluses, under-delivery, and/or cessation of fluid delivered to the patient Fluid supplies 38, 40, 42, and 44 (such as the fluid storage 120), which may take various forms but in this case are shown as bottles, are inverted and suspended above the pumps. Fluid supplies may also take the form of bags, syringes, or other types of containers. Both the patient care system 20 and the fluid supplies 38, 40, 42, and 44 may be mounted to a roller stand or intravenous (IV) pole 46.

A separate pump 22, 24, 26, and 28 may be used to infuse each of the fluids of the fluid supplies into the patient. The pumps 22, 24, 26, and 28 may be flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 7A. Many have check valves, drip chambers, valved ports, connectors, and other devices well known to those skilled in the art. These other devices have not been included in the drawings so as to preserve clarity of illustration. In addition, it should be noted that the drawing of FIG. 7A is not to scale and that distances have been compressed for the purpose of clarity. In an actual setting, the distance between the fluid supplies 38, 40, 42, and 44 and the pump modules 22, 24, 26, and 28 could be much greater.

Referring now to FIG. 7B, an enlarged view of the front of the patient care system 20 is shown. The pump 22 may include a front door 50 and a handle 52 that operates to lock the door in a closed position for operation and to unlock and open the door for access to the internal pumping and sensing mechanisms and to load administration sets for the pump. When the door is open, the tube (e.g., the fluid delivery tube 106) can be connected with the pump, as will be shown in FIG. 7C. When the door is closed, the tube is brought into operating engagement with the pumping mechanism, the upstream and downstream pressure sensors, and the other equipment of the pump. A display 54 (e.g., the display 154), such as an LED display, is located in plain view on the door in this embodiment and may be used to visually communicate various information relevant to the pump, such as alert indications (e.g., alarm messages). The display 54 may otherwise be a part of or be coupled to the pump 22. Control keys 56 exist for programming and controlling operations of the pump as desired. The pump 22 also includes audio alarm equipment in the form of a speaker (not shown).

In the embodiment shown, a programming module 60 is attached to the left side of the pump 22. In some embodiments, the programming module 60 forms a part of the pump 22. Other devices or modules, including another pump, may be attached to the right side of the pump 22, as shown in FIG. 7A. In such a system, each attached pump represents a pump channel of the overall patient care system 20. In one embodiment, the programming module is used to provide an interface between the pump 22 and external devices as well as to provide most of the operator interface for the pump 22.

The programming module 60 includes a display 62 for visually communicating various information, such as the operating parameters of the pump 22 and alert indications and alarm messages. The programming module 60 may additionally and/or alternatively communicate with the accessory system 102 to for, example, indicate that the predicted motor pressure and the measured fluid pressure have not converged (e.g., the error value is not less than the error threshold after a threshold number of cycles). The programming module 60 may additionally and/or alternatively display on the display 54, one or more parameters of the fluid, such as the fluid pressure, the patient pressure, and/or the motor pressure of the fluid in the fluid delivery tube (e.g. the fluid delivery tube 106). The programming module 60 may also include a speaker to provide audible alarms. The programming module or any other module also has various input devices in this embodiment, including control keys 64 and a bar code or other scanner or reader for scanning information from an electronic data tag relating to the infusion, the patient, the care giver, or other. The programming module also has a communications system (not shown) with which it may communicate with external equipment such as a medical facility server or other computer and with a portable processor, such as a handheld portable digital assistant ("PDA), or a laptop-type of computer, or other information device that a care giver may have to transfer information as well as to download drug libraries to a programming module or pump.

The communications system may take the form of a radio frequency ("RF") (radio frequency) system, an optical system such as infrared, a Bluetooth system, or other wired or wireless system. The bar code scanner and communications system may alternatively be included integrally with the pump 22, such as in cases where a programming module is not used, or in addition to one with the programming module. Further, information input devices need not be hard-wired to medical instruments, information may be transferred through a wireless connection as well.

FIG. 7B includes a second pump 26 connected to the programming module 60. As shown in FIG. 7A, more pump modules may be connected. Additionally, other types of modules may be connected to the pump modules or to the programming module.

Turning now to FIG. 7C, the pump 22 is shown in perspective view with the front door 50 open, showing the upstream fluid line 30 and downstream fluid line 31 in operative engagement with the pump 22. The pump 22 directly acts on a tube 66 (also referred to as a pump segment) that connects the upstream fluid line 30 to the downstream fluid line 31 to form a continuous fluid conduit, extending from the respective fluid supply 38 (FIG. 7A) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 22, such as the type described in co-pending U.S. patent application Ser. No. 13/827,775, which is incorporated by reference herein.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the fluid delivery tube until the next one in sequence has already occluded the fluid delivery tube; thus at no time is there a direct fluid path from the fluid supply to the patient. The operation of peristaltic pumps including four finger pumps is well known to those skilled in the art and no further operational details are provided here.

In this particular embodiment, FIG. 7C further shows a downstream pressure sensor 82 included in the pump 22 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 7A) and the flow control device, so that the connection of the correct fluid supply with the correct pump may be verified before any fluid is pumped to the patient. In some embodiments, the fluid pressure measured by the downstream pressure sensor 82 (which may include the sensor 110) may be filtered by an adaptive filter (e.g., the filter 104) to remove various components of the measured fluid pressure, such as the motor pressure caused by operation of the motor of the pump. This helps to improve feed-forward control of the pump and reduce unintended boluses, under-delivery, and/or cessation of fluid delivered to the patient With reference still to FIG. 7C, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 7A) and the flow control device, so that the connection of the correct fluid supply with the correct pump may be verified before any fluid is pumped to the patient. In an implementation where the source is a syringe, the flow control device 70 may be configured to press a plunger of the syringe to provide the infusion according to the programmed parameters.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together."

A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™ .NET™, web services, or rich site summary (RSS). In some embodiments, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some embodiments, include a signal utilized to transmit one or more representations of the information. While recited in the singular, it will be understood that a message may be composed, transmitted, stored, received, etc. in multiple parts.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:
   at least one data processor; and
   at least one memory storing instructions which, when executed by the at least one data processor, result in operations comprising:
   measuring, by a pressure sensor, a fluid pressure of fluid in a fluid supply line of an infusion pump, the fluid pressure comprising a motor pressure and a patient pressure, the motor pressure caused at least in part by a current of a motor of the infusion pump, and the patient pressure caused at least in part by movement of the patient;
   determining, by the at least one data processor, the patient pressure, the determining comprising removing, by a filter coupled to the pressure sensor and the at least one data processor, the motor pressure from the measured fluid pressure; and
   adjusting, based at least in part on the determined patient pressure, a setting of the infusion pump.

2. The system of claim 1, wherein the removing further comprises:
   generating a predicted motor pressure based on the current of the motor;
   generating an error signal based on a comparison between the predicted motor pressure and the measured fluid pressure; and
   removing the motor pressure from the measured fluid pressure when an error value representative of the error signal is less than an error threshold.

3. The system of claim 2, wherein the comparison between the predicted motor pressure and the measured fluid pressure is a difference between the predicted motor pressure and the measured fluid pressure.

4. The system of claim 2, wherein the error value is one or more of a norm of the error signal and a least means square of the error signal.

5. The system of claim 2, wherein generating the error signal further comprises applying a tap filter coefficient to the error value.

6. The system of claim 2, wherein the removing further comprises: determining whether the error value is less than the error threshold.

7. The system of claim 6, wherein the removing further comprises:
   determining that the error value is greater than or equal to the error threshold value; and
   adjusting one or more filter coefficients of the filter, the one or more filter coefficients applied to the current of the motor;
   generating an updated predicted motor pressure based on the adjusted one or more filter coefficients and the current of the motor.

8. The system of claim 7, wherein the removing further comprises:
   generating an updated error signal based on a comparison between the updated predicted motor pressure and the measured fluid pressure; and
   determining that an updated error value indicative of the updated error signal is less than the error threshold.

9. The system of claim 1, wherein the current of the motor is stored in a shift register of the filter.

10. The system of claim 1, wherein the filter is a variable digital adaptive filter.

11. The system of claim 1, further comprising:
   the filter; and
   the pressure sensor; wherein the at least one data processor comprises a controller.

12. A method, comprising:
   measuring, by a pressure sensor, a fluid pressure of fluid in a fluid supply line of an infusion pump, the fluid pressure comprising a motor pressure and a patient pressure, the motor pressure caused at least in part by a current of a motor of the infusion pump, and the patient pressure caused at least in part by movement of the patient;
   determining, by at least one data processor coupled to the pressure sensor, the patient pressure, the determining comprising removing, by a filter coupled to the pressure sensor and the at least one data processor, the motor pressure from the measured fluid pressure; and
   adjusting, by the at least one data processor based at least in part on the determined patient pressure, a setting of the infusion pump.

13. The method of claim 12, wherein the removing further comprises:
   generating a predicted motor pressure based on the current of the motor;
   generating an error signal based on a comparison between the predicted motor pressure and the measured fluid pressure; and
   removing the motor pressure from the measured fluid pressure when an error value representative of the error signal is less than an error threshold.

14. The method of claim 13, wherein the comparison between the predicted motor pressure and the measured fluid pressure is a difference between the predicted motor pressure and the measured fluid pressure.

15. The method of claim 13, wherein generating the error signal further comprises applying a tap filter coefficient to the error value.

16. The method of claim 13, wherein the removing further comprises: determining whether the error value is less than the error threshold.

17. The method of claim 16, wherein the removing further comprises:
   determining that the error value is greater than or equal to the error threshold value; and
   adjusting one or more filter coefficients of the filter, the one or more filter coefficients applied to the current of the motor;
   generating an updated predicted motor pressure based on the adjusted one or more filter coefficients and the current of the motor.

18. The method of claim 17, wherein the removing further comprises:
   generating an updated error signal based on a comparison between the updated predicted motor pressure and the measured fluid pressure; and
   determining an updated error value indicative of the updated error signal is less than the error threshold.

19. The method of claim 12, wherein the filter is a variable digital adaptive filter.

20. A non-transitory computer-readable storage medium including program code, which when executed by at least one data processor, cause operations comprising:
   measuring, by a pressure sensor, a fluid pressure of fluid in a fluid supply line of an infusion pump, the fluid pressure comprising a motor pressure and a patient pressure, the motor pressure caused at least in part by a current of a motor of the infusion pump, and the patient pressure caused at least in part by movement of the patient;
   determining, by at least one data processor coupled to the pressure sensor, the patient pressure, the determining comprising removing, by a filter coupled to the pressure sensor and the at least one data processor, the motor pressure from the measured fluid pressure; and
   adjusting, by the at least one data processor based at least in part on the determined patient pressure, a setting of the infusion pump.

* * * * *